(12) United States Patent
Whittall et al.

(10) Patent No.: US 6,673,936 B2
(45) Date of Patent: *Jan. 6, 2004

(54) PROCESS FOR PURIFYING 6-METHOXY OMEPRAZOLE

(76) Inventors: Linda B. Whittall, 2204 Splitbrook Ct., Wilmington, NC (US) 28411; Grayson Walker Stowell, 710 Darwin Dr., Wilmington, NC (US) 28405; Robert R. Whittle, 5006 Pine Needles Dr., Wilmington, NC (US) 28403

( * ) Notice: Subject to any disclaimer, the term of this patent is extended or adjusted under 35 U.S.C. 154(b) by 0 days.

This patent is subject to a terminal disclaimer.

(21) Appl. No.: 09/839,395
(22) Filed: Apr. 20, 2001
(65) Prior Publication Data US 2003/0088106 A1 May 8, 2003

(51) Int. Cl.[7] ............................................. C07D 401/00
(52) U.S. Cl. ..................................................... 546/273.4
(58) Field of Search ....................................... 546/273.4

(56) References Cited

FOREIGN PATENT DOCUMENTS

| WO | WO0114367 A1 | * | 3/2001 | |
| WO | WO 01/14367 | * | 3/2001 | |
| WO | WO01/14367 | | 3/2001 | .......... C07D/401/12 |

* cited by examiner

*Primary Examiner*—Alan L. Rotman
*Assistant Examiner*—Binta Robinson
(74) *Attorney, Agent, or Firm*—Myers Bigel Sibley & Sajovec, PA

(57) ABSTRACT

The present invention provides processes for purifying 6-methoxy omeprazole, products using such processes, pharmaceutical formulations using such products, and methods of using such products for gastric acid inhibition.

5 Claims, No Drawings

PROCESS FOR PURIFYING 6-METHOXY OMEPRAZOLE

BACKGROUND OF THE INVENTION

Until recently, omeprazole, the active ingredient in AstraZeneca's proton pump inhibitor commercially sold in the United States under the brand name Prilosec®, was chemically believed to be 5-methoxy-2-[[(4-methoxy-3,5-dimethyl-2-pyridinyl)methyl]sulfinyl]-1H-benzimidazole, in the solid state, represented by formula (1b):

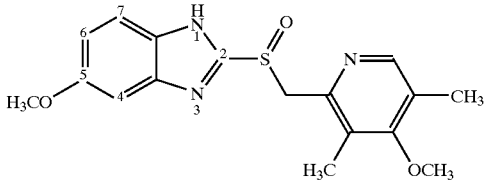

5-methoxy Omeprazole

However, Whittle, R. R., et al. disclosed in POT patent application WO 01/14367 that omeprazole, as a free base or as a salt, hydrate, or combination thereof, is actually two positional isomers co-crystallizing in a single crystalline lattice: the above-referenced 5-methoxy omeprazole represented by the formula (1b), and its preferred 6-methoxy isomer: 6-methoxy-2-[[(4-methoxy-3,5-dimethyl-2-pyridinyl)methyl]sulfinyl]-1H-benzimidazole, represented by formula (1a):

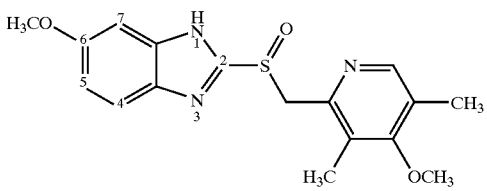

6-methoxy Omeprazole

Whittle, et al. further disclosed that the stability of omeprazole is affected by the ratio of 6-methoxy omeprazole to 5-methoxy omeprazole, with omeprazole being more favorably stable as the percentage of 6-methoxy omeprazole is increased. However, the processes presently available for preparing a higher percentage of the more preferred isomer, 6-methoxy omeprazole, and reduction in the 5-methoxy omeprazole percentage of the less preferred require controlling the rate of recrystallization, the solvent used, and other environmental factors. An alternative to the expensive and time-consuming method for increasing the percentage of 6-methoxy omeprazole in the crystalline lattice from an amount of 5(6)-methoxy omeprazole, would be technically and commercially beneficial.

SUMMARY OF INVENTION

Accordingly, the present invention provides methods for increasing the solid state percentage of 6-methoxy-2-[[(4-methoxy-3,5-dimethyl-2-pyridinyl)methyl]sulfinyl]-1H-benzimidazole, or a pharmaceutically acceptable salt, hydrate or combination thereof, from an amount of 5(6)-methoxy-2-[[(4-methoxy-3,5-dimethyl-2-pyridinyl)methyl] sulfinyl]-1H-benzimidazole, or a pharmaceutically acceptable salt, hydrate or combination thereof and, thus, also decreasing the percentage of 5-methoxy omeprazole proportionately.

DETAILED DESCRIPTION OF THE PREFERRED EMBODIMENTS

The present invention is described herein below in greater detail with reference to its preferred embodiments. These embodiments, however, are set forth to illustrate the invention and are not to be construed as a limitation thereof, the invention being defined by the claims.

It has been reported and further substantiated, that omeprazole API having higher percentages of 6-methoxy omeprazole compound relative to the respective 5(6)-methoxy omeprazole starting material typically provides greater stability, resulting in better commercial viability. Improved stability may also provide an improved safety profile via the minimization of degradants over time.

Accordingly, one aspect of the present invention provides processes for increasing, in the solid state, the percentage of a compound of formula (1a) compared to the percentage of such compound in co-crystallized (1a) and (1b) starting material (also known as omeprazole active pharmaceutical ingredient or "API"; and also referred to herein as 5(6)-methoxy-2-[[(4-methoxy-3,5-dimethyl-2-pyridinyl)methyl] sulfinyl]-1H-benzimidazole, or 5(6)-methoxy omeprazole or pharmaceutically acceptable salts, hydrates, or combinations thereof). As used herein, the compound represented by formula (1a) is also referred to as 6-methoxy omeprazole and the compound represented by formula (1b) is also referred to as 5-methoxy omeprazole.

As such, the starting material for the processes of the present invention is 5(6)-methoxy-2-[[(4-methoxy-3,5-dimethyl-2-pyridinyl)methyl]sulfinyl]-1H-benzimidazole, or pharmaceutically acceptable salts, hydrates, or combinations thereof. 5(6) methoxy omeprazole is prepared via various known methods including, for example, the methods described in PCT publication WO 01/14367 and U.S. Pat. No. 4,255,431.

In one embodiment, an amount of 5(6)-methoxy omeprazole is placed in a suitable container or, preferably, a Büchner funnel, to which is added an aliquot of short carbon chain ($C_1$–$C_4$) alcohol solvent including, for example, methanol, ethanol, and isopropyl alcohol, or a furan-based solvent such as, for example tetrahydrofuran ("THF"). THF has solvent properties similar to such short carbon chain alcohol solvents. Sufficient solvent is added to substantially cover and wet the starting material with gentle and thorough stirring. The solvent is then removed via methods known in the art, preferably under vacuum. As used herein, this process is referred to as "rinsing" the 5(6)-methoxy omeprazole API.

The amount of time required for such rinsing will typically be proportionate to the size of the starting material sample. In addition, the length of time the wetted material is stirred, as well as the percentage of 5-methoxy omeprazole in the starting material, can affect the final yield with longer wetting/stirring times providing potentially lower yields. As such, it may be better to minimize such wetting/stirring time, vacuum off the solvent, then re-rinse the starting material one or more times using the same procedure until the desired ratio of 6-methoxy omeprazole to 5-methoxy omeprazole is obtained.

Typically, this rinsing process is carried out at ambient temperature.

Unexpectedly, it was discovered that of the organic solvents examined, only THF and the short carbon chain alcohol solvents used in the processes of the present invention were capable of substantially selectively solubilizing the 5-methoxy omeprazole in the starting material, leaving a higher percentage of 6-methoxy omeprazole in the resulting product. Other solvents tested included, for example, ethyl acetate, isopropyl ether, acetone, acetonitrile, and water. Furthermore, it was discovered that the effectiveness of the rinsing process was directly related to the length of the carbon chain of such solvent, with the shorter chain alcohol solvents being preferred and methanol being especially preferred.

Accordingly, the rinsing portion of the instant process can last from about 5 seconds to about 30 seconds and more typically from about 10 seconds to about 20 seconds for small, test batches, and considerably longer as batch size increases.

The second step of the present process is drying the product from the rinse step. Generally, drying can be accomplished by a multitude of methods known to the ordinarily skilled artisan provided, if heat is used, the amount of heat used is insufficient to degrade or modify the product from the first step.

Typically, the product is placed in an appropriate, inert vessel, which is placed in a vacuum oven. Preferably, the oven is set at about 0 mm Hg and ambient temperature (about 25° C.) until the product is dry, although other conditions may possibly be employed. For small test samples, product is dried for about 24 hours, with drying time being increased for larger amounts of such product.

Preferably, the processes of the present invention provide 5(6)-methoxy omeprazole (or 6-methoxy omeprazole essentially devoid of 5-methoxy omeprazole) having a 5-methoxy percentage not greater than about ten percent of the sum of the total percentage of 5-methoxy omeprazole and 6-methoxy omeprazole. However, incremental reduction in the amount of 5-methoxy omeprazole compared to the respective starting material typically can provide improved stability attributes. As such, relative stability of the final product of the present processes increases as the percent of 5-methoxy omeprazole decreases, for example, from about 30% to about 25% to about 20% to about 15% to about 10% to about 5% to about 0%. Typically, the processes of the present invention are most effective at reducing the 5-methoxy omeprazole percentage to a range from about 6% to about 9%. Thus, processes of the present invention are most effective for reducing the level of 5-methoxy omeprazole in an amount of 5(6)-methoxy omeprazole when the percentage of such 5-methoxy omeprazole in the starting material is greater than about nine percent.

The measurement of the ratio of 5-methoxy omeprazole to 6-methoxy omeprazole in a given sample is best accomplished using Fourier Transform (FT) Raman Spectroscopy with methods as described in PCT publications WO 01/13919 and WO 01/14367. Such FT Raman methods can be abbreviated for in-process testing by reducing the number of replicates and scans per sample, recognizing that the optimal resolution set forth in the preferred embodiments of such PCT publications will not be obtained. Thus, abbreviated methods should only be used as estimates during process development or for in-process testing when optimal resolution is not required.

Another aspect of the present invention provides for 5(6)-methoxy omeprazole, or pharmaceutically acceptable salts, hydrates, or combinations thereof, when prepared by the process of the present invention. Preferably, such compounds comprise not more than about 9% of 5-methoxy omeprazole.

The present invention further provides pharmaceutical formulations, preferably in unit dosage form, comprising at least one compound prepared by the processes of the present invention, and at least one pharmaceutically acceptable carrier, diluent, excipient or combination thereof. Preferably, such at least one compound is pressed into tablets or encapsulated for oral administration. It is especially preferred to enterically coat such oral dosage forms. Methods for the preparation of oral dosage forms and preferred dosage strengths are as set forth, for example, in PCT publication WO 01/14367.

In addition, compounds of the present invention, preferably formulated into the above-referenced oral dosage forms, are effective for inhibiting gastric acid secretion in mammals and, thus are, beneficial for treating, preventing, or inhibiting disease states related to the secretion of gastric acids. Accordingly, the present invention provides a method of inhibiting gastric acid secretion in mammals, preferably humans, comprising administering to a mammal in need of treatment a therapeutically effective amount of a pharmaceutical formulation of the present invention.

The following examples are intended to illustrate the present invention and are not to be construed as limiting the scope of the present invention. As used herein, the phrase "5(6)-methoxy-2-[[(4-methoxy-3,5-dimethyl-2-pyridinyl) methyl]sulfinyl]-1H-benzimidazole, or its pharmaceutically acceptable salts, hydrates, or combinations thereof" refers to co-crystallized 5-methoxy-2-[[(4-methoxy-3,5-dimethyl-2-pyridinyl)methyl]sulfinyl]-1H-benzimidazole, or its pharmaceutically acceptable salts, hydrates, or combinations thereof, and 6-methoxy-2-[[(4-methoxy-3,5-dimethyl-2-pyridinyl)methyl]sulfinyl]-1H-benzimidazole, and its pharmaceutically acceptable salts, hydrates, or combinations thereof, respectively.

EXAMPLE 1

Preparation of 5(6)-methoxy-2-[[(4-methoxy-3,5-dimethyl-2-pyridinyl)methyl]sulfinyl]-1H-benzimidazole Having an Increased Amount of 6-methoxy-2-[[(4-methoxy-3,5-dimethyl-2-pyridinyl)methyl]sulfinyl]-1H-benzimidazole To a 50 mL ceramic Büchner funnel was added a sample of about 1.8 g of 5(6)-methoxy-2-[[(4-methoxy-3,5-dimethyl-2-pyridinyl)methyl]sulfinyl]-1H-benzimidazole having about 33% 5-methoxy-2-[[(4-methoxy-3,5-dimethyl-2-pyridinyl)methyl]sulfinyl]-1H-benzimidazole. To the sample was added 20 mL of methanol, and the sample was stirred until the sample was substantially covered and wetted. The mixture was allowed to sit for about 15 seconds, and the solvent was removed under vacuum at ambient temperature. To the resulting product was added an additional aliquot of 10 mL of methanol, and the sample was again stirred for about 15 seconds until the sample was again substantially covered and wetted. The additional solvent was again removed under vacuum at ambient temperature. The resulting product was completely dispensed into a 25 mL beaker that was placed in a vacuum oven set at 0 mm Hg and about 25° C. The product was dried for 24 hours. Yield of the title product was 49%, and the percentage of 6-methoxy-2-[[(4-methoxy-3,5-dimethyl-2-pyridinyl)methyl]sulfinyl]-1H-benzimidazole was increased from about 67% to about 91%.

EXAMPLE 2
Preparation of 5(6)-methoxy-2-[[(4-methoxy-3,5-dimethyl-2-pyridinyl)methyl]sulfinyl]-1H-benzimidazole Having an Increased Amount of 6-methoxy-2-[[(4-methoxy-3,5-dimethyl-2-pyridinyl)methyl]sulfinyl]-1H-benzimidazole The process in Example 1 was used except ethanol was used in lieu of methanol and the second aliquot of solvent added was 20 mL of ethanol. Yield of the title product was 65%, and the percentage of 6-methoxy-2-[[(4-methoxy-3,5-dimethyl-2-pyridinyl)methyl]sulfinyl]-1H-benzimidazole was increased from about 67% to about 76%.

EXAMPLE 3
Preparation of 5(6)-methoxy-2-[[(4-methoxy-3,5-dimethyl-2-pyridinyl)methyl]sulfinyl]-1H-benzimidazole Having an Increased Amount of 6-methoxy-2-[[(4-methoxy-3,5-dimethyl-2-pyridinyl)methyl]sulfinyl]-1H-benzimidazole The process in Example 1 was used except isopropyl alcohol was used in lieu of methanol, the second aliquot of solvent added was 20 mL of isopropyl alcohol, and 2.0 g of starting material was used. Yield of the title product was 85% and the percentage of 6-methoxy-2-[[(4-methoxy-3,5-dimethyl-2-pyridinyl)methyl]sulfinyl]-1H-benzimidazole was increased from about 67% to about 69%.

EXAMPLE 4
Preparation of 5(6)-methoxy-2-[[(4-methoxy-3,5-dimethyl-2-pyridinyl)methyl]sulfinyl]-1H-benzimidazole Having an Increased Amount of 6-methoxy-2-[[(4-methoxy-3,5-dimethyl-2-pyridinyl)methyl]sulfinyl]-1H-benzimidazole The process in Example 1 was used except tetrahydrofuran was used in lieu of methanol and the second aliquot of solvent added was 20 mL of tetrahydrofuran. Yield of the title product was 53% and the percentage of 6-methoxy-2-[[(4-methoxy-3,5-dimethyl-2-pyridinyl)methyl]sulfinyl]-1H-benzimidazole was increased from about 67% to about 73%.

We claim:

1. A method of substantially selectively solubilizing without dissolving and recrystallizing 5-methoxy-2-[[(4-methoxy-3,5-dimethyl-2-pyridinyl)methyl]sulfinyl]-1H-benzimidazole or a pharmaceutically acceptable salt, hydrate, or combination thereof from an amount of 5(6)-methoxy-2-[[(4-methoxy-3,5-dimethyl-2-pyridinyl)methyl]sulfinyl]-1H-benzimidazole or a pharmaceutically acceptable salt, hydrate, or combination thereof comprising:

(a) rinsing said amount of 5(6)-methoxy-2-[[(4-methoxy-3,5-dimethyl-2-pyridinyl)methyl]sulfinyl]-1H-benzimidazole with a solvent selected from the group consisting of a short carbon chain alcohol solvent and tetrahydrofuran; and (b) drying the product from step (a).

2. A method according to claim 1, wherein said short carbon chain alcohol solvent is selected from the group consisting of methanol, ethanol, and isopropyl alcohol.

3. A method according to claim 1, wherein said short carbon chain alcohol solvent is methanol.

4. A method according to claim 1 wherein said solvent is tetrahydrofuran.

5. A pharmaceutical formulation comprising 5(6)-methoxy-2-[[(4-methoxy-3,5-dimethyl-2-pyridinyl)methyl]sulfinyl]-1H-benzimidazole prepared by the methods claimed in any one of claims 1 through 4 in association with a pharmaceutically acceptable carrier, excipient or diluent.

* * * * *